United States Patent
Tiwari et al.

(10) Patent No.: US 10,906,866 B2
(45) Date of Patent: Feb. 2, 2021

(54) PROCESS FOR THE PREPARATION OF PHENOXYBENZAMINE

(71) Applicants: AUROBINDO PHARMA LIMITED, Hyderabad (IN); Shashi Kant Tiwari, Hyderabad (IN); Rajesh Chennuri, Hyderabad (IN); Bhanuchandar Samala, Hyderabad (IN); Venkata Ramana Kintali, Hyderabad (IN); Sivakumaran Meenakshisunderam, Hyderabad (IN)

(72) Inventors: Shashi Kant Tiwari, Hyderabad (IN); Rajesh Chennuri, Hyderabad (IN); Bhanuchandar Samala, Hyderabad (IN); Venkata Ramana Kintali, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 0 days.

(21) Appl. No.: 16/478,043

(22) PCT Filed: Jan. 10, 2018

(86) PCT No.: PCT/IB2018/050141
§ 371 (c)(1),
(2) Date: Jul. 15, 2019

(87) PCT Pub. No.: WO2018/130942
PCT Pub. Date: Jul. 19, 2018

(65) Prior Publication Data
US 2019/0359553 A1    Nov. 28, 2019

(30) Foreign Application Priority Data
Jan. 16, 2017 (IN) .............................. 201741001599

(51) Int. Cl.
*C07C 213/08* (2006.01)

(52) U.S. Cl.
CPC .................................. *C07C 213/08* (2013.01)

(58) Field of Classification Search
None
See application file for complete search history.

(56) References Cited

U.S. PATENT DOCUMENTS 2,599,000 A * 6/1952 Kerwin .............. C07D 295/088
564/353
2016/0095845 A1* 4/2016 Kwon ................ A61K 31/4453
514/317

\* cited by examiner

*Primary Examiner* — Clinton A Brooks
(74) *Attorney, Agent, or Firm* — PatentScience LLC; Jay R. Akhave

(57) ABSTRACT

The present invention provides a process for the preparation of N-phenoxyisopropyl ethanolamine of Formula (II) and its conversion to Phenoxybenzamine of Formula (I) or pharmaceutically acceptable salts thereof.

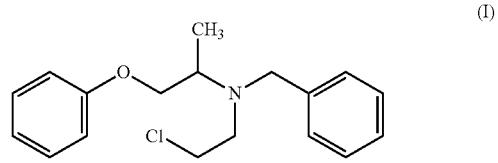

(I)

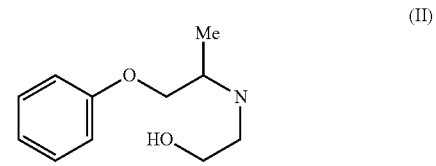

(II)

3 Claims, No Drawings

PROCESS FOR THE PREPARATION OF PHENOXYBENZAMINE

FIELD OF THE INVENTION

The present invention relates to a process for the preparation of N-phenoxyisopropyl ethanolamine of Formula (II) and its conversion to Phenoxybenzamine of Formula (I) or pharmaceutically acceptable salts thereof.

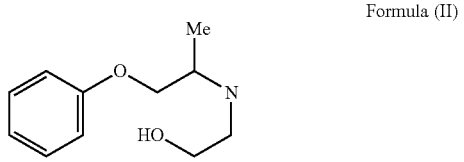

Formula (II)

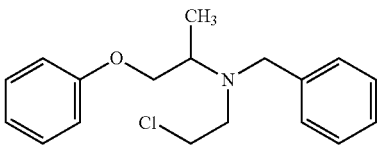

Formula (I)

BACKGROUND OF THE INVENTION

Phenoxybenzamine hydrochloride (I) is chemically known as N-(2-Chloroethyl)-N-(1-methyl-2-phenoxyethyl) benzylamine hydrochloride and is marketed under the brand name Dibenzyline®. Dibenzyline® is a long-acting, adrenergic, alpha-receptor blocking agent, which can produce and maintain "chemical sympathectomy" by oral administration. Phenoxybenzamine hydrochloride (I) is an Antihypertensive drug indicated in the treatment of pheochromocytoma, to control episodes of hypertension and sweating.

Phenoxybenzamine hydrochloride (I) is disclosed first time in U.S. Pat. No. 2,599,000. This patent also discloses a process for the preparation of Phenoxybenzamine hydrochloride starting from 1-phenoxy-2-propanol.

The above process is as shown in Scheme-I below:

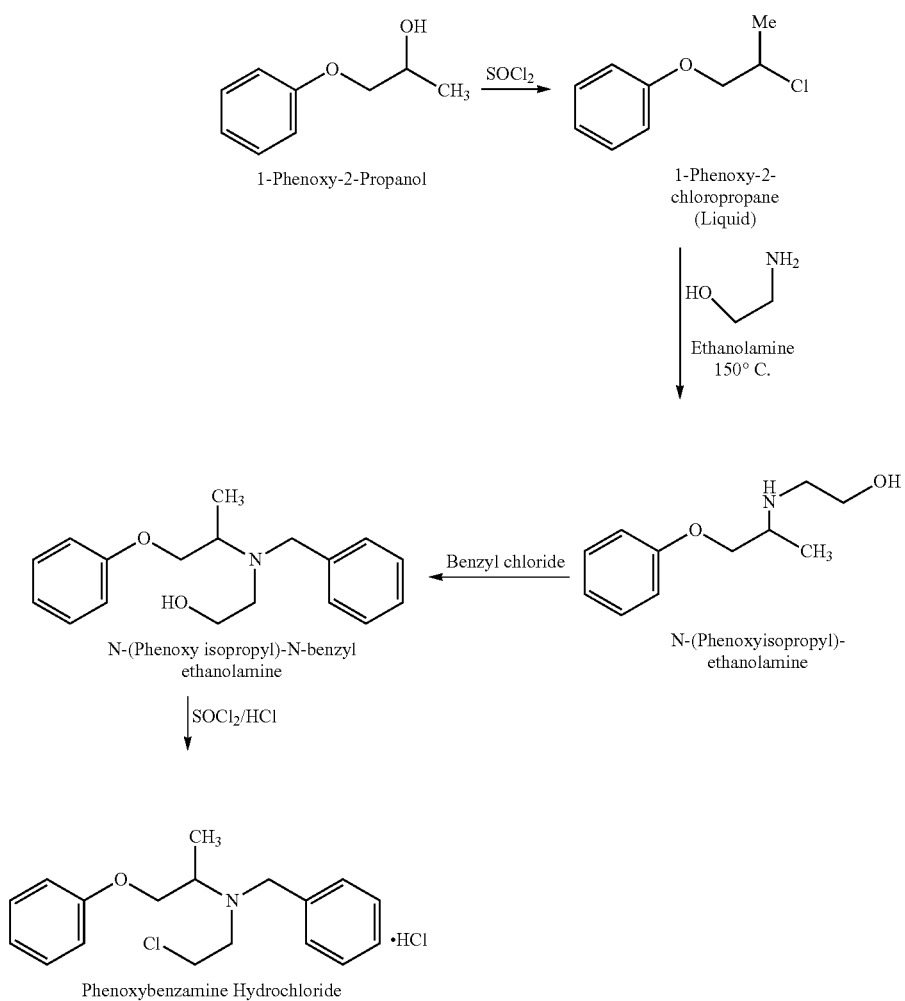

Scheme-I

CN 102675132 A discloses a similar process for the preparation of Phenoxybenzamine hydrochloride (I).
The process is as shown in Scheme-II below:

Scheme-II

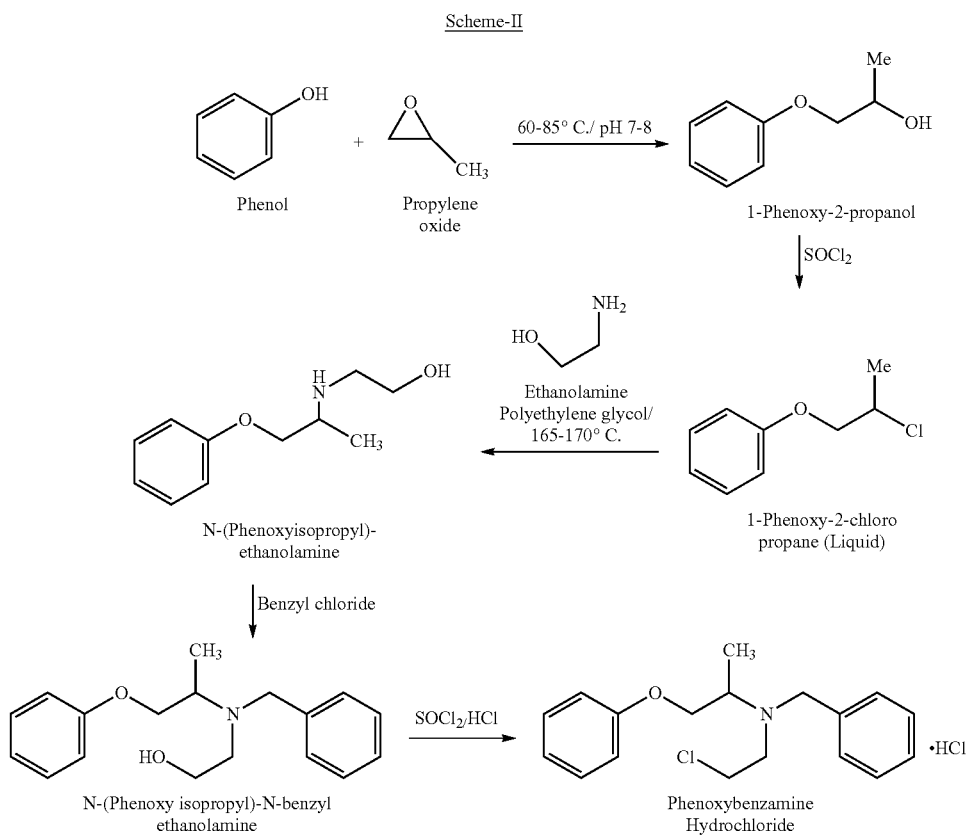

The major drawbacks associated with the prior-art processes of Phenoxybenzamine is the coupling of 1-Phenoxy-2-chloropropane (liquid compound) with ethanolamine takes place only at high temperatures in the range of ≥150° C. which makes the process not viable for large scale operations.

Hence, there is a need of an improved process for the preparation of Phenoxybenzamine or pharmaceutically acceptable salts which not only devoid the disadvantage of the prior process as mentioned herein above but also gives high purity of Phenoxybenzamine or pharmaceutically acceptable salts. The process of the present invention overcomes the above disadvantages and gives high purity of Phenoxybenzamine or pharmaceutically acceptable salts.

OBJECTIVE OF THE INVENTION

The objective of the present invention is to provide a process for the preparation of N-phenoxyisopropyl ethanolamine of Formula (II) with high purity and its conversion to Phenoxybenzamine of Formula (I) or pharmaceutically acceptable salts thereof with high purity.

SUMMARY OF THE INVENTION

In an embodiment, the present invention provides a process for the preparation of N-phenoxyisopropyl ethanolamine of Formula (II) or salt thereof:

Formula (II)

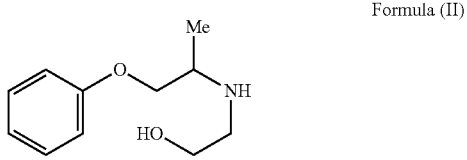 [SMILES: CC(COc1ccccc1)NCCO]

which comprises reacting a compound of Formula (III);

Formula (III)

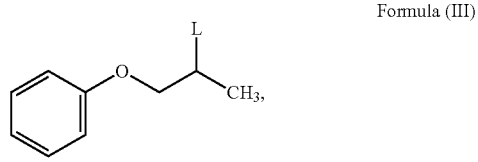

wherein, L is a leaving group, with mono ethanolamine to obtain N-phenoxyisopropyl ethanolamine of Formula (II).

In another embodiment, the present invention provides a process for the preparation of N-phenoxyisopropyl ethanolamine of Formula (II) or salt thereof, which comprises reacting a compound of Formula (IIIa) or salt thereof;

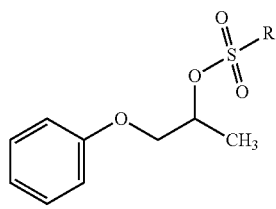

Formula (IIIa)

wherein R is $C_{1-12}$ straight or branched-chain alkyl, $C_{2-12}$ cyclo alkyl, $C_{6-12}$ aryl and each hydrogen in R is optionally substituted with one or more halogen or $C_{1-6}$ straight or branched-chain alkyl;
with mono ethanolamine to obtain N-phenoxyisopropyl ethanolamine of Formula (II).

In another embodiment, the present invention provides a process for the preparation of Phenoxybenzamine of Formula (I) or pharmaceutically acceptable salts thereof;

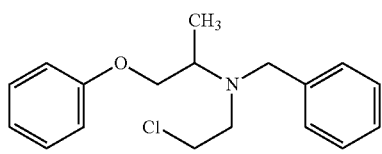

Formula (I)

which comprises:
a. protecting 1-phenyl-2-propanol of Formula (IV) or salt thereof;

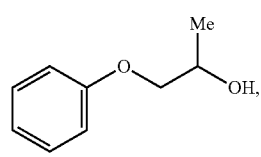

Formula (IV)

with sulfonic acid derivatives to obtain a compound of Formula (IIIa) or salt thereof;

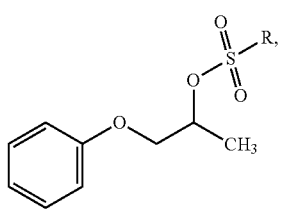

Formula (IIIa)

wherein, R is as defined above;
b. reacting a compound of Formula (IIIa) or salt thereof with mono ethanolamine to produce N-phenoxyisopropyl ethanolamine of Formula (II) or salt thereof;

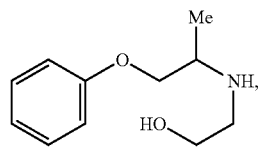

Formula (II)

c. reacting the compound of Formula (II) or salt thereof with benzyl chloride to obtain N-(phenoxyisopropyl)-N-benzylethanolamine of Formula (I-A) or salt thereof;

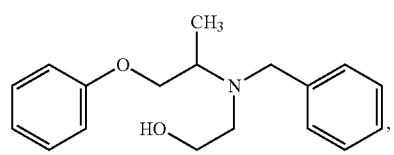

Formula (I-A)

d. reacting the compound of Formula (I-A) or salt thereof with a chlorinating agent to obtain Phenoxybenzamine of Formula (I) or pharmaceutically acceptable salt thereof.

DETAILED DESCRIPTION OF THE INVENTION

The present invention relates to process for the preparation of N-phenoxyisopropyl ethanolamine of Formula (II) or salt thereof:

The process comprises, reacting compound of Formula (III) with mono ethanolamine to obtain N-phenoxyisopropyl ethanolamine of Formula (II) or salt thereof.

The leaving group 'L' of Formula (III) is selected from fluoro, bromo, iodo, nitro, thioether, phosphate, carboxylate, phenoxide, alkoxide, amide, mesylate and tosylate.

The compound of Formula (III) can be prepared by using the process of the present invention. The compound of Formula (III) or salt thereof can be used as crystalline or amorphous.

The reaction of compound of Formula (III) with mono ethanolamine is performed in the presence or absence of solvent. The suitable solvent is selected from polar protic solvent comprises water, methanol, ethanol, isopropanol, n-butanol, and/or mixtures thereof; polar aprotic solvent comprises dimethylformamide (DMF), dimethylsulfoxide (DMSO), tetrahydrofuran (THF), acetonitrile, acetone, ethyl acetate, N-methyl pyrrolidone and/or mixtures thereof; and non-polar solvents comprises hexane, benzene, toluene, 1,4-dioxane, chloroform, diethyl ether, dichloromethane ($CH_2Cl_2$) or mixtures thereof.

The reaction is conducted at a temperature of about 75° C. to 150° C. without affecting the quality of product. The reaction is carried out for a period of about 30 minutes to about 3 hours or more to complete the reaction.

The resultant compound of Formula (II) is used directly to prepare Phenoxybenzamine of Formula (I) or pharmaceutically acceptable salt thereof without isolating or isolated by using techniques of distillation, recrystallization, anti-solvent and the like.

The present invention also relates to a process for the preparation of N-phenoxyisopropyl ethanolamine of Formula (II), which comprises the reaction of compound of Formula (IIIa) or salt thereof with mono ethanolamine.

The compound of Formula (IIIa) is prepared and isolated using the process of present invention.

The inventors of the present invention found that the reaction of compound of Formula (IIIa) with monoethanolamine is performed without a solvent to obtain N-phenoxyisopropyl ethanolamine of Formula (II) or salt thereof with higher yield and purity.

The suitable temperature for conducting the above reaction is about 75° C. to 150° C., preferably in the range from about 100° C. to about 120° C.

After completion of the reaction, the reaction mixture is cooled and subjected for isolation of Formula (II) using suitable techniques such as recrystallization, distillation, adding anti-solvent and the like.

The present invention also relates to a process for the isolation of N-phenoxyisopropyl ethanolamine of Formula (II) or salt thereof by extraction of reaction mixture of Formula (II) or salt thereof into organic solvent followed by concentration and precipitation of solid from ether solvent.

The reaction mixture of Formula (II) obtained from the present invention is subjected for extraction of Formula (II) into organic solvent using water and organic solvent. The organic solvent is selected from chlorinated solvent, for example, dichloromethane, dichloroethane, chloroform, and the like; ester solvent, for example, ethyl acetate, isopropyl acetate and the like.

The organic layer containing Formula (II) is concentrated using distillation and evaporation technique to obtain crude, which is then, crystallized from ether solvent such as diisopropyl ether, methyl tertiary butyl ether (MTBE) and the like.

The resultant compound of Formula (II) of the present invention is having the purity greater than of about 99% by HPLC and the yield of about 80 to about 90%.

The present invention also relates to a process for the preparation of Phenoxybenzamine (I) or pharmaceutically acceptable salts thereof by protecting 1-phenyl-2-propanol (IV) or salt thereof with sulfonic acid derivatives to obtain a compound of Formula (IIIa) or salt thereof followed by reacting with mono ethanolamine in the absence of solvent to produce N-phenoxyisopropyl ethanolamine (II) or salt thereof which is then reacted with benzyl chloride to obtain N-(phenoxyisopropyl)-N-benzylethanolamine (I-A) or salt thereof and then treated with chlorinating agent to obtain Phenoxybenzamine of Formula (I) or pharmaceutically acceptable salts thereof.

The overall process of the present invention is depicted in Scheme III of below:

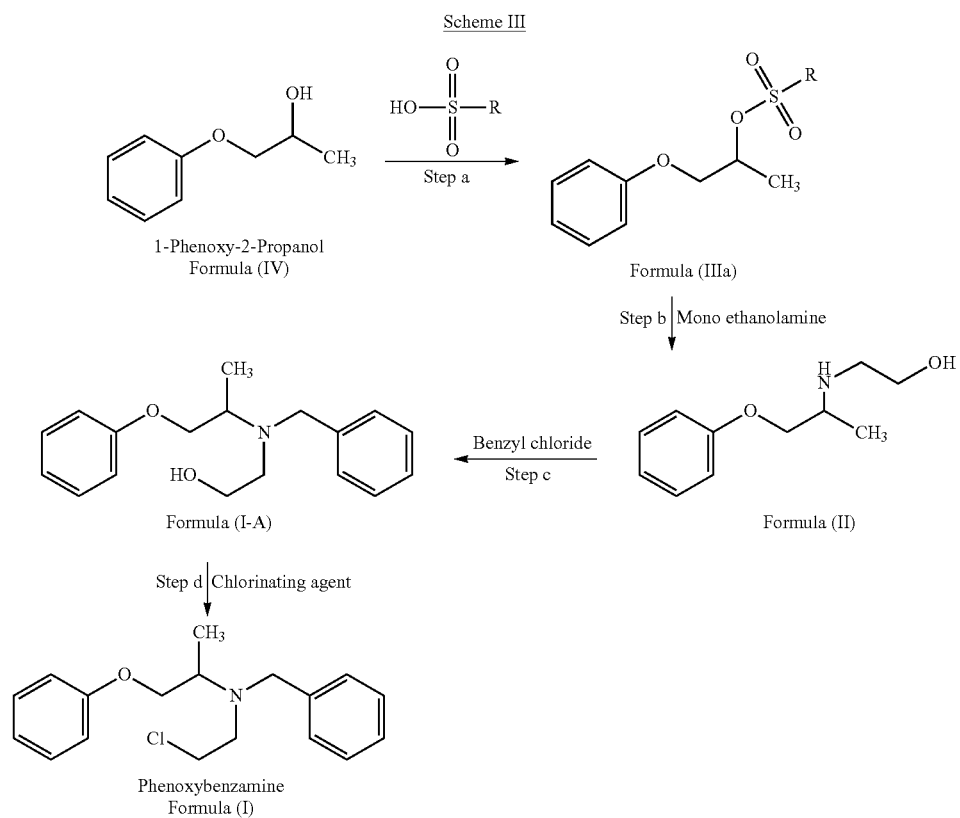

The step a) involves reaction of 1-phenyl-2-propanol (IV) with sulfonic acid derivative in the presence of a base and a solvent to obtain a compound of Formula (IIIa).

The base used in step a) is selected from organic or inorganic base wherein organic base is selected from N,N-diisopropylethylamine, triethylamine, triisopropylamine, N,N-2-trimethyl-2-propanamine, N-methylmorpholine, pyridine and 4-dimethylaminopyridine and inorganic base is selected from lithium hydroxide, sodium hydroxide, potassium hydroxide, magnesium hydroxide, calcium hydroxide, sodium carbonate, potassium carbonate, calcium carbonate, sodium bicarbonate and potassium bicarbonate.

The solvent used in the present invention comprises of polar protic solvent or polar aprotic solvent or non-polar solvent and/or mixture thereof.

In an embodiment suitable chlorinating agent is selected from thionyl chloride, phosphorus pentachloride, phosphoryl chloride, phosgene, oxalyl chloride or triphenylphosphine dichloride.

The pharmaceutically acceptable salt or salt of the present invention can be selected from inorganic acid salt or organic acid salt. Examples of suitable inorganic acids include hydrochloric acid, hydrobromic acid, phosphoric acid, sulfuric acid, and perchloric acid. Examples of suitable organic acids include acetic acid, oxalic acid, maleic acid, tartaric acid, citric acid, succinic acid, formic acid and malonic acid.

The following examples illustrate the nature of the invention and are provided for illustrative purposes only and should not be construed to limit the scope of the invention.

EXAMPLES

Example 1: Synthesis of 1-phenoxypropane-2-yl-4-methylbenzene sulfonate 1-phenoxy-2-propanol (50.0 g; 328.94 mmol) in dichloromethane (250 mL) at 25-30° C. was added to triethylamine (99.75 g; 987.62 mmol) and dimethylamino pyridine (DMAP) (4.0 g; 32.78 mmol). Then the resulting reaction mixture was cooled to 10-15° C. and added P-Toluene sulfonylchloride (75.0 g; 394.73 mmol). The reaction mixture was stirred at 30-35° C. for 6-7 hours, filtered the solid product and washed with chilled MTBE followed by drying at 40-50° C. under reduced to afford 1-phenoxypropane-2-yl-4-methylbenzene sulfonateas off yellow to pale brown color solid. (72.13% yield; >98% HPLC purity)

Example 2: Synthesis of N-(phenoxyisopropyl)-ethanolamine

Mono ethanolamine (30.0 g; 0.491 moles) and 1-Phenoxypropane-2-yl-4-methylbenzene sulphonate (50.0 g; 0.163 moles) were heated to 110-115° C. and stirred for 2 hours. Then the reaction mass cooled to 30-35° C. and dichloromethane (100 ml) and D.M. water (50 ml) were added while stirring. Organic layer was concentrated under reduced at 30-35° C. and the obtained residue was dissolved in MTBE and allowed to cool to obtain the solid product which was filtered and dried under vacuum at 45-50° C. to afford N-(phenoxyisopropyl)-ethanolamine. (77% yield; >98% HPLC purity)

Example 3: Synthesis of N-(phenoxyisopropyl)-N-benzyl Ethanolamine

N-(phenoxy isopropyl)-ethanolamine (95.0 g; 0.487 moles) in ethanol (475 ml) and sodium bicarbonate (82.0 g) were added to benzyl chloride (80.1 g; 0.976 moles) at 25-30° C. The obtained reaction mixture was heated to reflux for 20 hours at 78-80° C. then concentrated under reduced pressure and residue was dissolved in dichloromethane (475 ml) and was concentrated at 30-35° C. to obtain crude oily liquid (160.0 g) of N-(phenoxyisopropyl)-N-benzyl ethanolamine.

Example 4: Synthesis of N-(2-Chloroethyl)-N-(1-methyl-2-phenoxy ethyl)

benzylamine hydrochloride (Phenoxybenzamine Hydrochloride); N-(phenoxyisopropyl)-N-benzyl ethanolamine was dissolved in dichloromethane (810 ml) at 25-30° C. and slowly added thionyl chloride (70.0 g; 0.588 moles) at 0-5° C. The reaction mass was stirred at 25-30° C. for 2 hours and concentrated under reduced pressure at 30-35° C. and residue was dissolved in acetone (570 ml) at 25-30° C. for solid formation. Filtered the solid and washed with chilled acetone (190 ml) and was dried at 45-50° C. under vacuum to get 125.4 g of pure Phenoxybenzamine hydrochloride as a white solid (HPLC purity>99%).

We claim:
1. A process for the preparation of N-phenoxyisopropyl ethanolamine of Formula (II) or salt thereof;

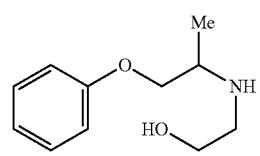

Formula (II)

which comprises reacting a compound of Formula (IIIa);

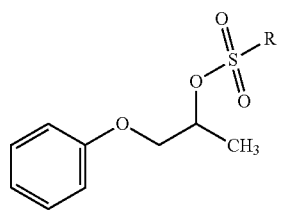

Formula (IIIa)

wherein R is $C_{1-12}$ straight or branched-chain alkyl, $C_{2-12}$ cyclo alkyl, $C_{6-12}$ aryl and each hydrogen in R is optionally substituted with one or more halogen or $C_{1-6}$ straight or branched-chain alkyl;
with mono ethanolamine to obtain N-phenoxyisopropyl ethanolamine of Formula (II).

2. A process for the preparation of Phenoxybenzamine of Formula (I) or pharmaceutically acceptable salts thereof:

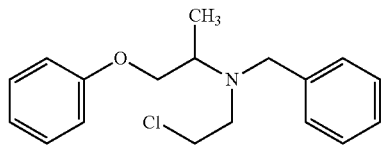

Formula (I)

which comprises:
a. further reacting the compound of Formula (II) or salt thereof prepared as claimed in claim 1, with benzyl chloride to obtain N-(phenoxyisopropyl)-N-benzylethanolamine of Formula (I-A) or salt thereof;

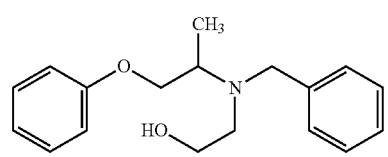

Formula (I-A)

b. reacting the compound of Formula (I-A) or salt thereof with a chlorinating agent to obtain Phenoxybenzamine of Formula (I) or pharmaceutically acceptable salt thereof.

3. The process as claimed in claim 2, wherein the chlorinating agent used in step (b) is selected from thionyl chloride, phosphorus pentachloride, phosphoryl chloride, phosgene, oxalyl chloride or triphenylphosphine dichloride.

* * * * *